United States Patent [19]
Winkler

[11] Patent Number: 6,047,864
[45] Date of Patent: Apr. 11, 2000

[54] ACTUATING DEVICE

[75] Inventor: Siegbert Winkler, Feldkirch, Austria

[73] Assignee: Lvoclar AG, Schaan, Liechtenstein

[21] Appl. No.: 09/072,011

[22] Filed: May 4, 1998

[30] Foreign Application Priority Data

Jun. 18, 1997 [DE] Germany .......................... 197 25 863

[51] Int. Cl.[7] .................................................. G01F 11/00
[52] U.S. Cl. .............................. 222/326; 222/567; 433/90
[58] Field of Search ..................................... 222/326, 386, 222/474, 567; 433/90

[56] References Cited

U.S. PATENT DOCUMENTS

| | | | |
|---|---|---|---|
| 4,198,756 | 4/1980 | Dragan | 222/326 |
| 4,295,828 | 10/1981 | Rudler. | |
| 4,472,141 | 9/1984 | Dragan. | |
| 5,743,431 | 4/1998 | Brattesani | 222/326 |
| 5,918,772 | 7/1999 | Keller et al. | 222/567 |

FOREIGN PATENT DOCUMENTS

0 063 891 A1  11/1982  European Pat. Off. .

Primary Examiner—Philippe Derakshani
Attorney, Agent, or Firm—John C. Thompson; Alan S. Korman

[57] ABSTRACT

An actuating device for dispensing of a paste-like material, especially in the dental field, from a capsule or cartridge has an abutment for the support of the capsule or cartridge at the actuating device in the direction of dispensing. The abutment is provided at a collar-shaped projection and is a part of at least one securing tongue. The securing tongues are provided at the housing of the actuating device and can be released for releasing the capsule or cartridge.

21 Claims, 5 Drawing Sheets

ACTUATING DEVICE

BACKGROUND OF THE INVENTION

The present invention relates to an actuating device for dispensing a paste-like material, especially in the dental field, from a capsule or cartridge, whereby the actuating device has an abutment for supporting the capsule or cartridge within the actuating device in the direction of dispensing.

Such an actuating device is known from U.S. Pat. No. 4,472,141. This actuating device comprises a handle which acts on a plunger by which a paste-like material for dental purposes is dispensed from a capsule or cartridge. According to U.S. Pat. No. 4,472,141, a threadable closure cap and an undercut in the form of a counter collar are provided at the capsule or cartridge which are connected to the forward end of the actuating device. The force to be applied by the handle onto the plunger and thus onto the capsule or cartridge is, in general, a multiple of the manual force applied whereby due to the selected leverage ratio, for example, five times the manual force is applied to the paste-like material.

Since the spacing between the pressure application of the handle and its pivot axis surpasses the spacing between the pivot axis and the follower of the plunger, for example, by a factor 5, the applied plunger force can thus have a magnitude of one kN or even more. With respect to this force, there is the risk that the capsule or cartridge will break out of the comparatively thin screw cap or will deform in the area of the counter collar such that a safe supporting action is no longer possible. This is true especially when the screw cap is not securely applied because then it is not ensured that the capsule or cartridge is properly supported with its counter collar between the undercut of the screw cap and a sealing ring or the forward end of the exterior thread. On the other hand, when manipulating the actuating device It is not always detectable whether the screw cap has been completely secured.

Another actuating device Is known from European Patent Application A1-63 891. This actuating device comprises a downwardly open channel in which the cartridge is secured. The cartridge is oversized relative to the sidewalls of the channel and, accordingly, the channel should be somewhat flexible in order to be able to introduce the cartridge from the open side.

This arrangement, however, has not been proven successful in practice. Due to the tight guiding of the counter collar within the channel, which is required for reasons of stability, the cartridge upon removal must be guided exactly parallel to the axis of the plunger present in the device. However, since it can be gripped only at its forward end, there is always the risk that the cartridge upon removal will jam and the counter collar of the cartridge will become jammed in the guide. The user then assumes that an increased actuating force must be applied which he can do without a problem, but will result in that the cartridge can break, resulting in undesirable contamination of the actuating device as well as of the surroundings. This is especially a problem when mercury-containing amalgam materials are used as a paste-like material in the dispensing or actuating device.

It is therefore an object of the present invention to provide an actuating device of the aforementioned kind which allows a safe actuation at high actuating forces with easy removal of the capsule or cartridge.

SUMMARY OF THE INVENTION

The actuating device for dispensing a paste material from a cartridge according to the present invention is primarily characterized by:

a housing having a forward and a rearward end;

the housing accommodating a cartridge containing a paste material at the forward end;

a plunger slidably arranged in the rearward end of the housing and acting on the cartridge for dispensing the paste material when actuated;

a pivot handle pivotably connected to the housing for actuating the plunger;

at least one securing tongue connected to the housing;

the at least one securing tongue releasably securing the cartridge at the housing; and the at least one securing tongue comprising a projecting collar having an abutment for supporting the cartridge in a dispensing direction.

Between two and four the securing tongues are preferably present.

The actuating device may further comprise a slide sleeve moveably supported at the housing and having a securing position in which the cartridge is secured in the housing and a release position in which the cartridge is released from the housing.

In the securing portion of the slide sleeve the abutment secures the cartridge by engaging a counter abutment of the cartridge to thereby prevent the cartridge from being forced out of the housing when the plunger is actuated.

The cartridge has a plunger and the plunger of the housing acts on the plunger of the cartridge in order to dispense the paste material.

In the release position of the slide sleeve the cartridge Is ejected from the housing by actuating the handle and the plunger of the housing.

The projecting collar has a radial extension that is greater than a radial extension of the counter abutment of the cartridge.

The projecting collar has a slanted surface opposite the abutment, wherein the slanted surface is directed radially inwardly and facilitates insertion of the cartridge into the housing by spreading the securing tongues radially outwardly.

The slide sleeve is preferably held in the release position and in the securing position by a frictional connection or a snap connection.

The cartridge has a counter abutment. In the securing position of the slide sleeve, the cartridge is slidable in the housing whereby a travel stroke of the cartridge is limited by the counter abutment.

The slide sleeve in the securing position supports a radially outer surface of the securing tongues.

The slide sleeve in the securing position is positioned radially outwardly of the projecting collar and overlaps partially the projecting collar.

The projecting collar extends at least over a portion of its radial extension at a slant forwardly at an angle of 70° to a longitudinal axis of the housing.

The securing tongues are preferably unitary parts of the housing and are radially outwardly prestressed and tensioned by the slide sleeve in the securing position.

The slide sleeve has a first thickened portion at a forward end and a second thickened portion at a rearward end and further has an annular grip depression between the first and second thickened portions.

The slide sleeve has an inner bevel at the forward end.

The counter abutment has an axial length that is greater than a wall thickness of the cartridge, preferably, the axial length is twice the wall thickness.

The actuating device may further comprise a locking member for locking in the release position the plunger of the cartridge, wherein the locking member is a locking tongue acting, depending on a position of the slide sleeve, as a alternative to the abutment and the projecting collar.

The cartridge comprises a counter abutment engaging behind the projecting collar.

The counter abutment is overlapped by the slide sleeve in the securing position such that the slide sleeve projects forwardly past a contact surface for the abutment.

The inventive actuating device allows for a safe securing due to the unitary construction of the shaft of the actuating device and the collar-shaped projection provided as an abutment for securing the capsule or cartridge. This allows sliding of the slide sleeve into a locking position in which it surrounds the securing area of the tongues for supporting the capsule or cartridge so that a safe support is ensured because the spring-elastic tongues cannot move. On the other hand, the locking position can be easily recognized based on the position of the slide sleeve.

Furthermore, this invention surprisingly allows for the possibility to remove the completely empty capsule or cartridge from the actuating device by employing the handle of the actuating device after release of the slide sleeve. Since the actuating force applied by the handle onto the cartridge is substantially greater than the manually applied force, this solution allows for a comparatively stiff embodiment of the projections (projecting collars) provided for anchoring and also for the embodiment of the abutments at a slanted position close to 90°.

The invention is also advantageous with respect to a constructively clean separation between the spring function for releasing and introducing the cartridge, on the one hand and the securing function via the stiff slide sleeve, on the other hand.

According to a further advantageous embodiment, it is suggested that a plurality of tongues extends annularly about the capsule or cartridge. The tongues end in a thickened portion which radially inwardly forms the collar-shaped projection (projecting collar) and radially outwardly provides an abutment for the slide sleeve. The radially inwardly oriented projection extends to the exterior wall of the capsule or cartridge so that the capsule or cartridge is supported at the projection in the radial direction and is guided in the axial direction. This provides for the possibility to guide the cartridge in a slidable manner axially into the end position which is defined by the abutment between the collar-shaped projection and the counter collar. Since the cartridge comprises a slantedly extending outlet, the movability in the rearward direction is limited by the outlet abutting the forward end of the respective tongue. In the securing position the slide sleeve is axially positioned such that the rearward end of the capsule or cartridge projects considerably. However, there is no overlap between the slide sleeve and the capsule or cartridge in the release position of the slide sleeve. It is preferred that in this position a considerable radial spacing is provided.

The relative dimensions in the radial direction allow for adjusting whether the contact between actuating device and cartridge is realized between the exterior wall of the cartridge and the projection at the tongues or between the outer surface of the counter collar (counter abutment) and the inner surface of the tongue or at both locations. In order to ensure a large support area, it is preferred to provide the contact location between the projection of the tongues and the exterior surface of the cartridge.

The tongues at their forward ends have preferably an inner bevel or radially Inwardly oriented slanted surfaces which facilitate introduction of the cartridge when the slide sleeve is in the release position.

BRIEF DESCRIPTION OF THE DRAWINGS

The object and the advantages of the present invention will appear more clearly from the following specification in conjunction with the accompanying drawings, in which.

DESCRIPTION OF PREFERRED EMBODIMENTS

The present invention will now be disclosed in detail with the aid of the embodiments of FIGS. 1 through 12.

Figure 1:
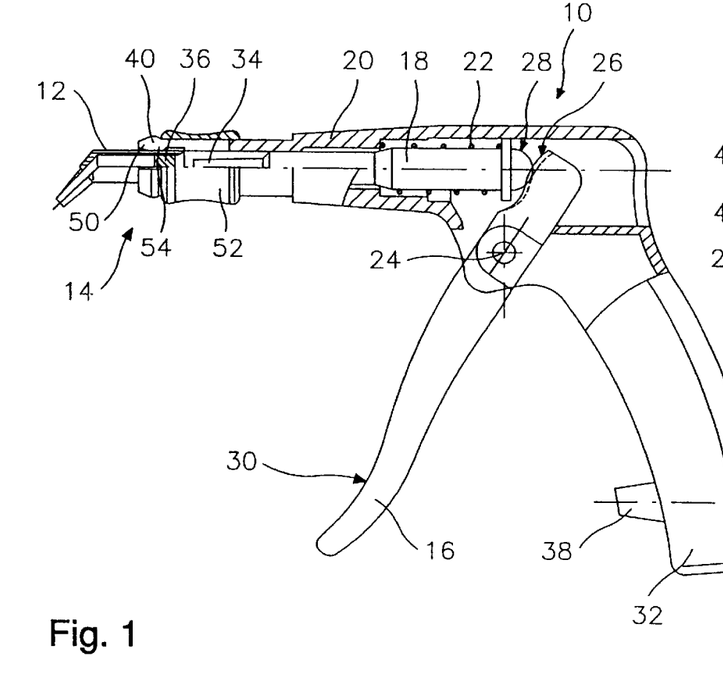
FIG. 1 shows a part-sectional side view of one embodiment of the inventive actuating device.

The shown embodiment of the actuating device 10 represented in FIG. 1 is suitable for dispensing dental materials (pastes) and Is embodied in the form of an injector. The device 10 secures a capsule or cartridge 12 at its forward end 14. The actuating device has a handle 16 which acts on a plunger 18. The plunger 18 is movably supported within the housing 20 of the actuating device 10 and is elastically tensioned by a pressure spring 22 in the direction of the handle. The handle 16 is pivotably supported at a pivot pin 24, and acts with its curved or spherical pressure surface 26 onto the plunger 18 which also has a curved or spherical pressure surface 28 able to slide or glide along the pressure surface 26.

The spacing between the pressure surfaces 26 and 28 and the bearing pin 24 that provides the pivot axis for the grip 16 is substantially smaller than the spacing between the actuating depression 30 of the handle 16. The ratio of the spacing is approximately 1:5 so that onto the plunger 18 almost 5 times the force of the manual force applied on the grip 16 is provided. The actuating device 10 is essentially pistol-shaped so that already the basic design results in an ergonomic actuation and favorable force transmission for movement of the handle 16 toward the pistol grip 32. The applied force is transmitted by the plunger tip 34 onto the cartridge 12.

The cartridge 12 comprises a plunger 36 onto which the tip 34 acts. The outer diameter of the tip 34 is somewhat smaller than the diameter of the plunger 36 so that the tip 34 can enter the cartridge 12 and is able to dispense the dental material contained in the cartridge 12 via the force applied by the plunger 36. The dental material is not represented in the Figures.

Figures 4, 6:
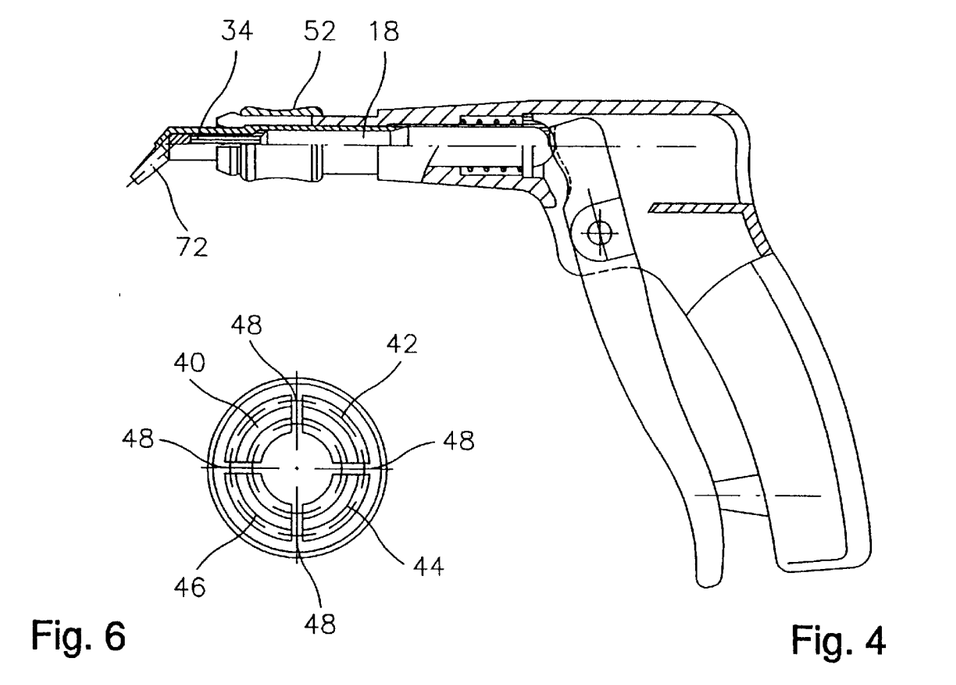
FIG. 4 shows the actuating device according to FIG. 1 illustrating the position of the handle in the actuated positions.
FIG. 6 shows a schematic front view of the actuating device with representation of the tongues.
Figure 5:
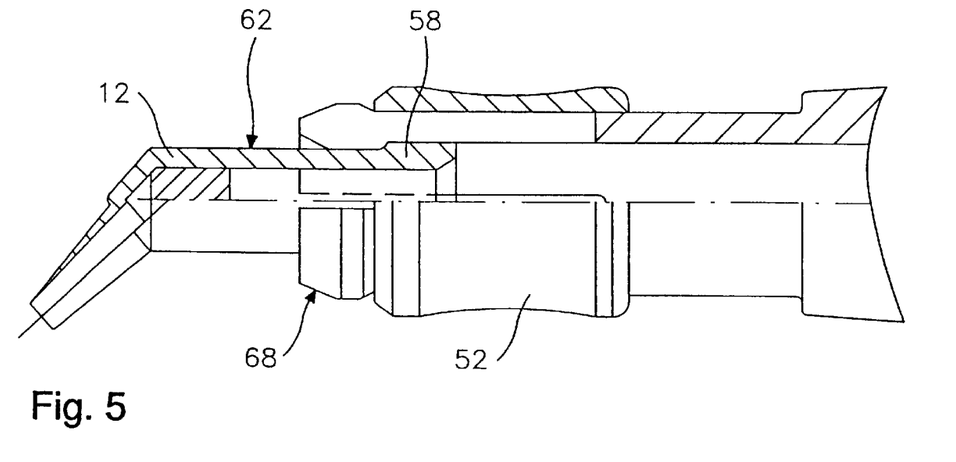
FIG. 5 shows an enlarged detail of the embodiment shown in FIG. 4

As can be seen when comparing the representation of FIGS. 1 and 4, the handle 16 for dispensing the dental material can be pivoted from a left into a right end position. In the right end position the handle 16 rests at the stop 38 which serves as a travel limiter. From this position, the plunger 18 is moved toward the left, i.e., toward the forward end 14 of the housing 20, whereby the pressure spring 22 is compressed. The plunger 18 tapers in a stepped manner to the forward end whereby in the shown embodiment two steps are provided.

Figure 2:
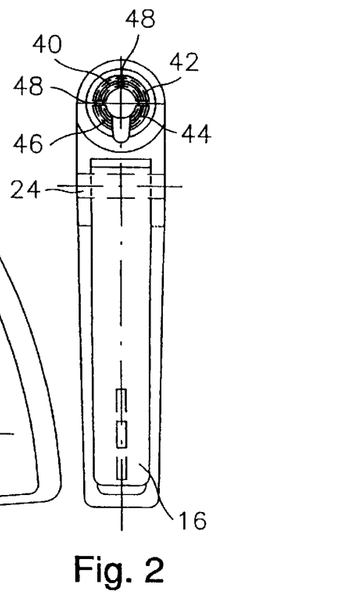
FIG. 2 shows the embodiment according to FIG. 1 in a view from the left, i.e., a view of the actuating device from the front.
Figure 3:
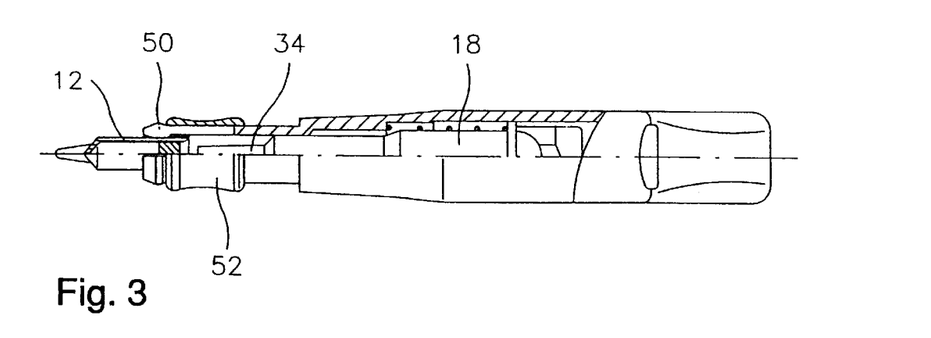
FIG. 3 shows a part-sectional view of the actuating device according to FIG. 1.

At the forward end 14 the housing 20 has a plurality of securing tongues 40 to 46 which can be seen especially well in FIG. 2. Each securing tongue 40 to 46 extends approximately about a quarter circle about the cartridge circumference. Between them slots 48 are provided which provide for an elastic embodiment of the tongues. The tongues 40–46 end in a thickened portion 50 which extends radially inwardly as well as outwardly. The radially outer projection of the thickened portion 50 provides an abutment for the movement of a slide sleeve or clamping bushing 52 which can be moved between a securing position, represented in FIG. 1, and a release position, represented in FIG. 7. In the securing position the slide sleeve 52 overlaps the tongues 40 to 46 up to the thickened portion 50, while in the release position according to FIG. 7 the tongues are substantially free over their entire length and are thus spring-elastic and movable.

The slide sleeve 52 prevents in the securing position a radial movement of the tongues 40 to 46 because it surrounds the tongues in an annular configuration.

A respective collar-shaped projection (projecting collar) 54 extends radially inwardly from the thickened portion 50. The design of the collar-shaped projection is represented in detail in FIGS. 5, 8, and 9 so as to provide a better illustration. At its rearward end the projecting collar 54 provides an abutment 56 for the cartridge 12. The cartridge 12 at its rear end has a counter collar (counter abutment) 58 which extends radially outwardly.

The radial extension of the counter collar 58 is somewhat smaller than that of the projecting collar 54 so that the surface 60 of the projection (projecting collar) 54 pointing radially inwardly provides a gliding surface for the outer surface 62 of the cartridge 12. The cartridge 12 in the shown embodiment is slidable in the axial direction whereby the contact between the abutment 56 and the counter collar 58 delimits the movement in the forward direction.

The abutment 56 in the shown embodiment has a slanted surface having an angle of slant of approximately 70° relative to the axis 64 of the housing 20 of the actuating device. This slanted surface allows, on the one hand, a safe support of the securing position of the slide sleeve 62 and, and on the other hand, a removal or forcing-out of the cartridge 12 in the release position of the slide sleeve 52. For removing or pressing-out the cartridge, the tongues 40 to 46 are spread by the slanted abutments 56 to such an extent that the slots 48 are widened and the counter collar 58 can be positioned within the area of the surface 60. In this spread position of the tongue 40 to 46 the cartridge 12 can be easily removed.

Figure 9:
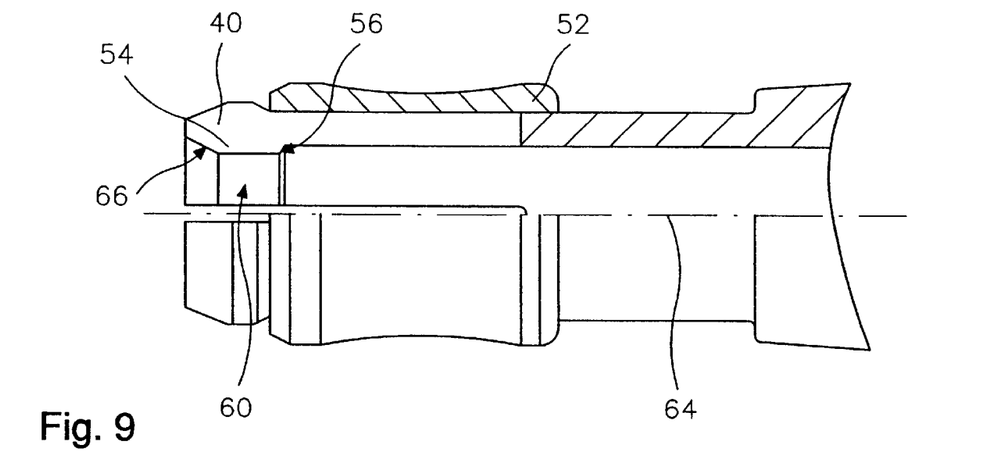
FIG. 9 shows an enlarged representation of the forward portion of the inventive actuating device, the cartridge not being represented.
Figure 10:
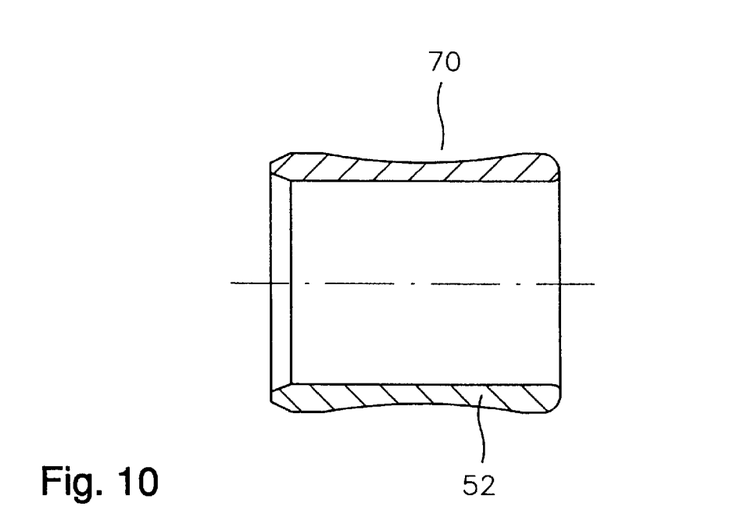
FIG. 10 shows the slide sleeve for the inventive actuating device.

The projections 54, as can be seen especially in FIG. 9, have at their forward end an insertion slant 66. The insertion slant 68 points radially inwardly and serves for spreading the tongues 40 to 46 upon insertion of the cartridge 12 in the release position of the slide sleeve 52. The degree of slant of the insertion slant 66 is substantially flatter than the degree of slant of the abutment 56 since for the insertion of the cartridge 12 the handle 16 and the plunger 18 must not be available for applying an auxiliary force, but the cartridge 12 must instead be manually inserted.

The counter collar 58 occupies a comparatively large axial length of the cartridge radius. Even for a certain elastic deformation in the removal direction the counter collar 58 thus remains as a safe abutment despite the comparatively minimal radial dimension of the abutment 56 as well as of the counter collar 58. This design is favorable with respect to the slim design concept of the inventive actuating device and of the inventive injector.

The inventive embodiment is especially advantageous with respect to the relatively small number of parts which are securely attached to one another so that they are suitable for a safe and reliable operation even for very viscous materials while realizing a slim actuating device. While in the shown embodiment the radial extension of the thickened portion, which has adjacent to the insertion slant 66 at its forward radially outward pointing end a bevel 68, corresponds approximately to the radius of the cartridge 12. It is understood that a modified embodiment also allows considerably reduced or enlarged dimensions.

It is especially favorable that in the represented embodiment in the securing position of the slide sleeve 52, the slide sleeve 52 projects as an extension of the very flat bevel that extends, for example, at an angle of 20° relative to the axis 64 and does not project to the exterior. This facilitates manipulation. However, the slide sleeve 52 provides a wide grip depression 70 which can been seen especially in FIG. 10.

As can be seen in FIG. 4, the plunger 18, in the position farthest to the left, can move with its forward end 34 the plunger 36 to such an extent in the forward direction that it abuts the forward end of the cartridge 12 so that only the area of the outlet 72 is still filled with the visceus material.

Figure 7:
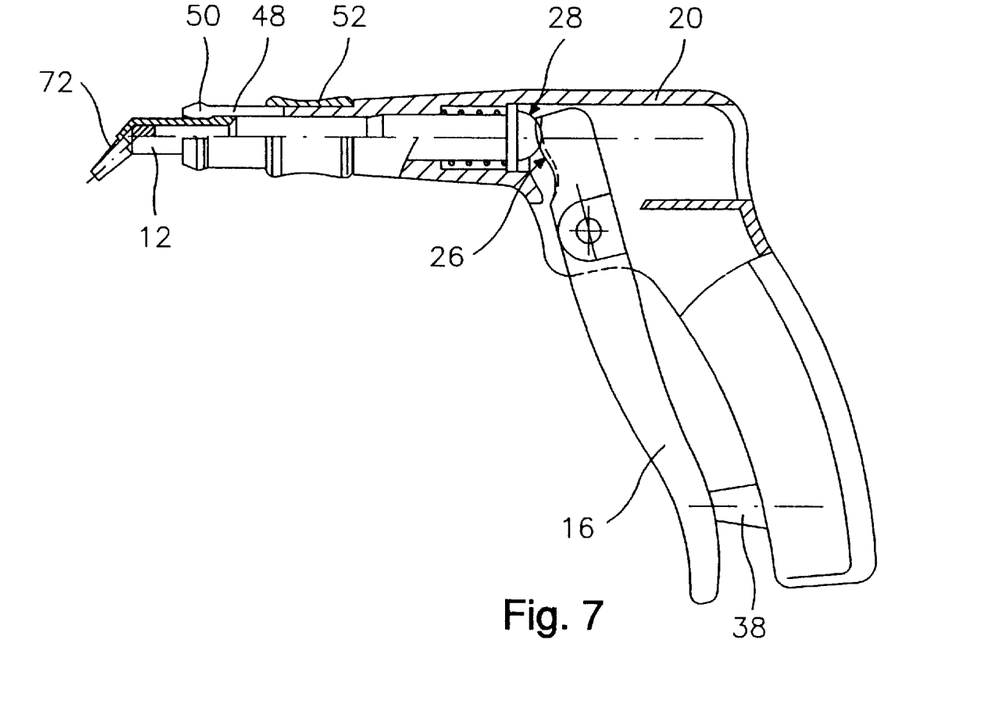
FIG. 7 shows a view according to the representation of FIG. 4 whereby the slide sleeve is in the release position.

For removing the cartridge, the slide sleeve 52 is moved to the right in FIG. 7 so that it is in the release position. It is advantageous when the stop 38 is slightly elastic so that by a slight pressure applied via the handle 16 and the plunger 18 onto the plunger 36, resting already at the forward end of the cartridge 12, the spreading resistance of the tongues Is overcome by cooperation of the abutment 56 and the counter collar 58, and the empty cartridge 12 can then be manually easily removed.

The inventive actuating device is characterized furthermore by allowing for dispensing of the viscous material, for example, a dental material, in a single dispensing step but also in any desired number of steps. When the dental material is dispensed in a plurality of steps, as a function of the required amount, an easy manipulation is provided in that the handle 16 is returned into its initial position by the pressure spring 22. The user actuates, for example, for a half-empty cartridge 12 the handle again up to half of the actuating travel whereby the tip 34 of the plunger 18 is then in contact at the plunger 36 and a resistance can be felt. Upon further actuation of the handle 16, the dental material is then dispensed until the cartridge 12 is empty. In this position, the handle 16 rests at the stop 38 and the cartridge 12 can then be removed as disclosed above by applying only a manual force via the handle 16.

Figure 8:
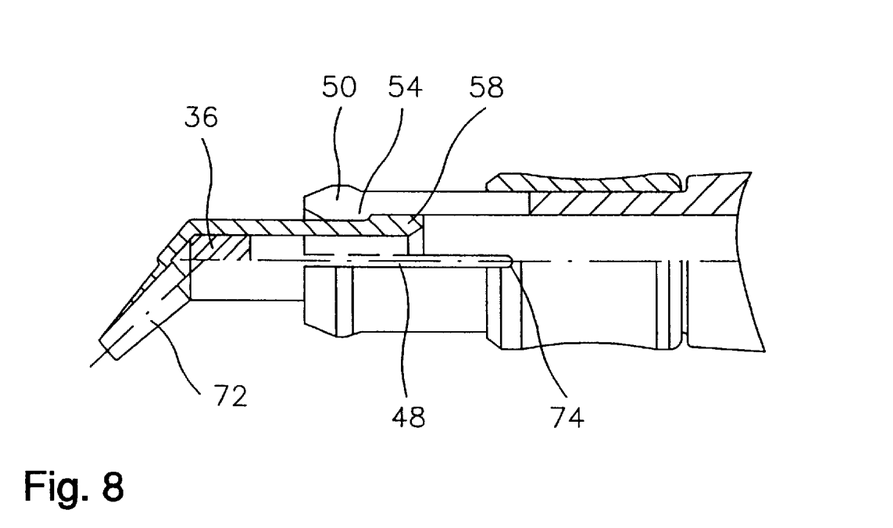
FIG. 8 shows a view according to FIG. 5, whereby the slide sleeve is in its release position.

As can be seen in FIG. 8, the slots 48 end at their rearward end in a radius 74. Even for frequent spreading of the tongues, an actuation without notching, and thus a long service life and operation of the inventive actuating device, is ensured.

Figure 11:
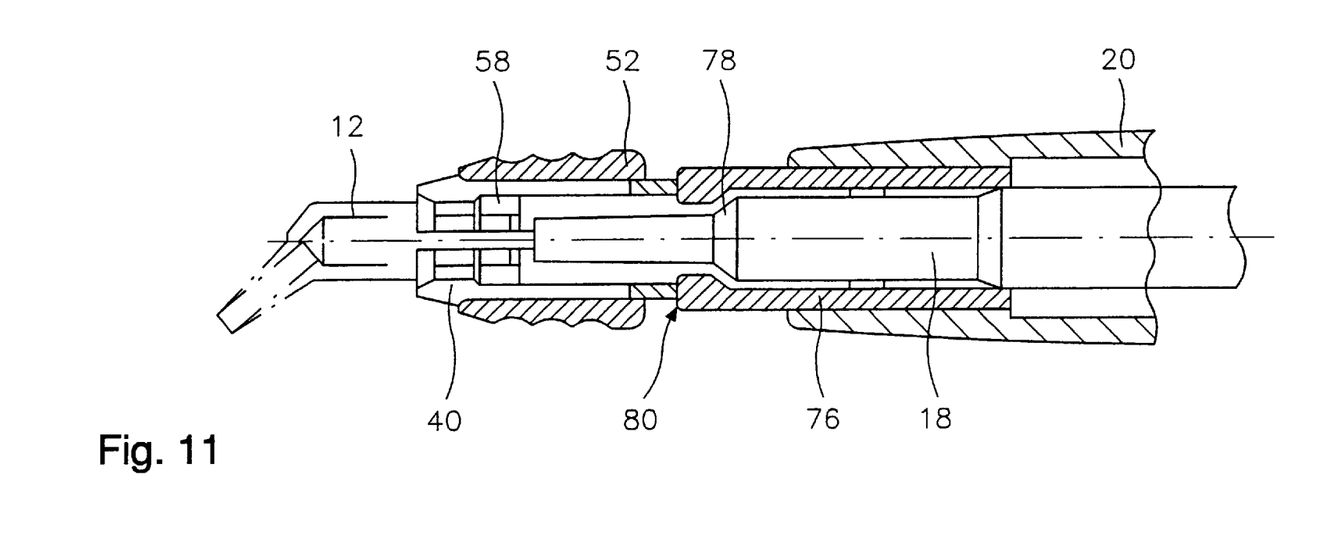
FIG. 11 shows a representation of the front portion of the inventive actuating device in a second embodiment.
Figure 12:
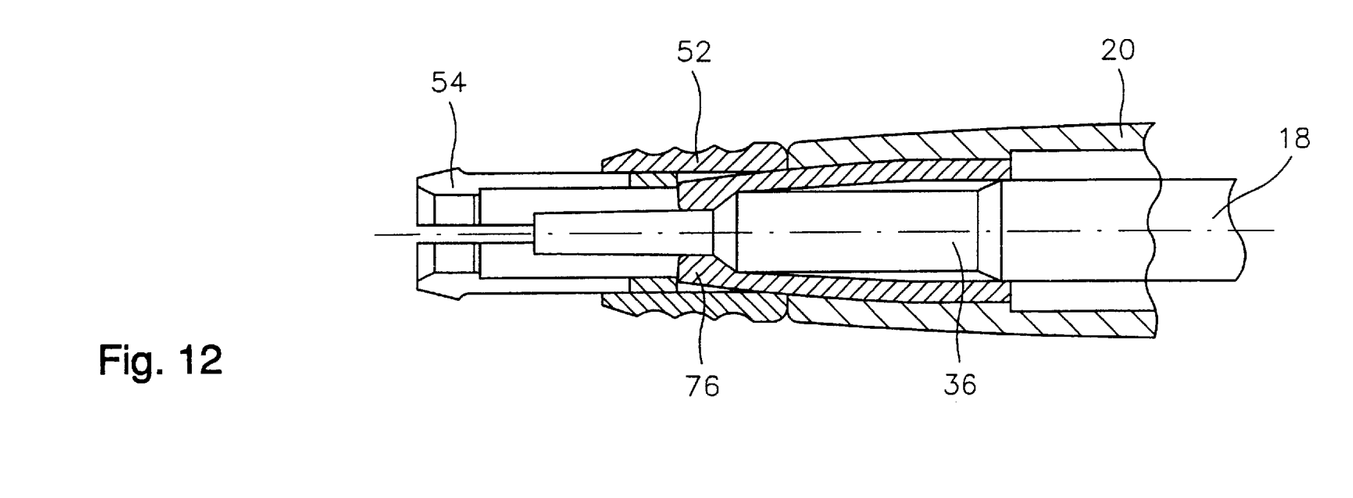
FIG. 12 shows a representation of the second embodiment according to FIG. 11 whereby the capsule is removed and the slide sleeve is in its release position.

A further embodiment of the inventive actuating device is shown in FIG. 11 and 12. FIG. 11 shows the sleeve 52 in the securing position for the cartridge 12 so that, in analogy to the representation of FIG. 1, 4, and 5, the counter collar 58 is secured in a form-locking manner by the projecting collar 54 and the capsule 12 cannot be pressed out by the pressure force of the plunger 18 from the actuating device.

In this position, tongue or plier-shaped locking members are not functioning. They are arranged, in the return position of the plunger 18, in the area of but in front of the step 78 of the plunger 18 whereby the radial extension of the locking member 76 is selected such that the plunger 18 can be freely moved, even with its greater diameter adjacent to the step 78, and will not be locked by the locking members 76.

The locking members 76 are provided at tongues connected to the housing 20 which, in analogy to the tongues 40 to 46, are moveable in their forward area. Two oppositely arranged tongues are provided whereby the housing 20 projects past the locking members 76 in the forward direction. The locking members 76 have at their forward/outer ends an insertion slant 80 for the slide sleeve 52. Upon return movement of the sleeve 52, i.e., upon sliding into the release position, the sleeve 52 compresses the locking members 76 radially inwardly so that they move toward one another with their inwardly positioned projections and provide a diameter which is smaller than the diameter of the plunger 18 in the area adjacent to the step 78.

This position is shown in FIG. 12.

When comparing FIGS. 11 and 12, the sleeve 52 thus secures either the tongues 40 to 46 so that they cannot be moved outwardly or the tongue-shaped locking members 76 so that they cannot move outwardly whereby the respective other tongues are released.

This inventive embodiment has the advantage that a dentist cannot accidentally forget, after insertion of the capsule or cartridge 12, to move the sleeve 52 forwardly. It is thus ensured that the capsule cannot accidentally be ejected at high pressure in the forward direction so that any risk of injury is thus prevented. In practice, the actuation of the actuating device is locked as long as the sleeve 52 has not been moved into the securing position.

The present invention is, of course, in no way restricted to the specific disclosure of the specification and drawings, but also encompasses any modifications within the scope of the appended claims.

What is claimed is:

1. An actuating device for dispensing a paste material from a cartridge, said actuating device comprising:

a housing having a forward and a rearward end;

said housing accommodating a cartridge containing a paste material at said forward end;

a plunger slidably arranged in said rearward end of said housing and acting on the cartridge for dispensing the paste material when actuated;

a pivot handle pivotably connected to said housing for actuating said plunger;

at least one securing tongue connected to staid housing;

said at least one securing tongue releasably securing the cartridge at said housing; and said at least one securing tongue comprising a projecting collar having an abutment for supporting the cartridge in a dispensing direction.

2. An actuating device according to claim 1, wherein between two and four of said securing tongues are present.

3. An actuating device according to claim 1, further comprising a slide sleeve moveably supported at said housing and having a securing position in which the cartridge is secured in said housing and a release position in which the cartridge is released from said housing.

4. An actuating device according to claim 3, wherein in said securing portion of said slide sleeve said abutment secures the cartridge by engaging a counter abutment of the Cartridge to thereby prevent the cartridge from being forced out of said housing when said plunger is actuated.

5. An actuating device according to claim 3, wherein the cartridge has a plunger and wherein said plunger of said housing acts on the plunger of the cartridge in order to dispense the paste material.

6. An actuating device according to claim 3, wherein in said release position of said slide sleeve the cartridge is ejected from said housing by actuating said handle and said plunger of said housing.

7. An actuating device according to claim 4, wherein said projecting collar has a radial extension that is greater than a radial extension of the counter abutment of the cartridge.

8. An actuating device according to claim 1, wherein said projecting collar has a slanted surface opposite said abutment, wherein said slanted surface is directed radially inwardly and facilitates insertion of the cartridge into said housing by spreading said securing tongues radially outwardly.

9. An actuating device according to claim 3, wherein said slide sleeve is held in said release position and in said securing position by a frictional connection or a snap connection.

10. An actuating device according to claim 3, wherein the cartridge has a counter abutment and wherein in said securing position of said slide sleeve said cartridge is slidable in said housing whereby a travel stroke of the cartridge is limited by the counter abutment.

11. An actuating device according to claim 3, wherein said slide sleeve in said securing position supports a radially outer surface of said securing tongues.

12. An actuating device according to claim 11, wherein said slide sleeve in said securing position is positioned radially outwardly of said projecting collar and overlaps partially said projecting collar.

13. An actuating device according to claim 1, wherein said projecting collar extends at least over a portion of its radial extension at a slant forwardly at an angle of 70° to a longitudinal axis of said housing.

14. An actuating device according to claim 3, wherein said securing tongues are unitary parts of said housing and are radially outwardly prestressed and tensioned by said slide sleeve in said securing position.

15. An actuating device according to claim 3, wherein said slide sleeve has a first thickened portion at a forward end and a second thickened portion at a rearward end and further has an annular grip depression between said first and second thickened portions.

16. An actuating device according to claim 15, wherein said slide sleeve has an inner bevel at said forward end.

17. An actuating device according to claim 4, wherein said counter abutment has an axial length that is greater than a wall thickness of the cartridge.

18. An actuating device according to claim 17, wherein said axial length is twice said wall thickness.

19. An actuating device according to claim 3, further comprising a locking member for locking in said release position the plunger of the cartridge, wherein said locking member is a locking tongue acting, depending on a position of said slide sleeve, as a alternative to said abutment and said projecting collar.

20. A cartridge for an actuating device according to claim 3, wherein said cartridge comprises a counter abutment engaging behind said projecting collar.

21. A cartridge according to claim 20, wherein said counter abutment is overlapped by said slide sleeve in said securing position such that said slide sleeve projects forwardly past a contact surface for said abutment.

* * * * *